United States Patent [19]

Barger

[11] Patent Number: 5,248,647
[45] Date of Patent: Sep. 28, 1993

[54] SAPO CATALYSTS AND USE THEREOF IN METHANOL CONVERSION PROCESSES

[75] Inventor: Paul T. Barger, Arlington Heights, Ill.

[73] Assignee: UOP, Des Plaines, Ill.

[21] Appl. No.: 793,874

[22] Filed: Dec. 23, 1991

Related U.S. Application Data

[62] Division of Ser. No. 662,076, Feb. 28, 1991, Pat. No. 5,095,163.

[51] Int. Cl.$^5$ .................. B01J 29/04; B01J 27/182
[52] U.S. Cl. .................................................. 502/214
[58] Field of Search ...................... 502/64, 85, 214; 423/308, 328

[56] References Cited

U.S. PATENT DOCUMENTS

| | | | |
|---|---|---|---|
| 4,681,864 | 7/1987 | Edwards et al. | 502/64 |
| 4,803,185 | 2/1989 | Miller et al. | 502/64 |
| 4,814,316 | 3/1989 | Pellet et al. | 502/64 |

*Primary Examiner*—Carl F. Dees
*Attorney, Agent, or Firm*—Thomas K. McBride; Richard G. Miller

[57] ABSTRACT

Hydrothermal treatment of silicoaluminophosphate molecular sieves at temperatures in excess of about 700° C. for periods sufficient to destroy a large proportion of their acid sites while retaining at least 80 percent of their crystallinity is found to result in a catalyst for converting methanol to lower olefins having increased catalyst life, increased selectivity for $C_2$-$C_3$ olefins and decreased selectivity for paraffin production than the untreated SAPO-n starting composition.

4 Claims, No Drawings

SAPO CATALYSTS AND USE THEREOF IN METHANOL CONVERSION PROCESSES

This application is a division of Ser. No. 07/622,076 filed Feb. 28, 1991 and now U.S. Pat. No. 5,095,163.

FIELD OF THE INVENTION

The present invention relates in general to the catalytic conversion of methanol to olefins and, more particularly, to processes for converting methanol to olefins using a catalyst composition comprising a silicoaluminophosphate which has been modified by steaming to eliminate a significant percentage of its acid sites while maintaining at least 80 percent of its as-synthesized crystallinity. The invention also relates to the catalyst composition per se and to the method for its preparation.

BACKGROUND OF THE INVENTION

The conversion of methanol to olefin-enriched or gasoline boiling range hydrocarbons using solid microporous molecular sieves is well known in the art. Such conversions using aluminosilicate, i.e., zeolitic, molecular sieve catalysts, are disclosed in U.S. Pat. Nos. 4,238,631; 4,328,384 and 4,423,274. The zeolite catalysts of these patented processes have pore diameters of about 6 Angstroms, a pore size believed to be too large for optimal olefin production. For that reason, a high coke level was maintained on the catalyst as a means of diminishing the effective pore diameters of the zeolites. In U.S. Pat. No. 4,079,095 the catalyst proposed for utilization in the conversion of methanol to light olefins is the relatively small pore zeolite ZSM-34. This particular zeolite did not benefit in olefin selectivity from being coked.

It has also been proposed to utilize certain of the aluminophosphate-based molecular sieves as catalysts for the conversion of alcohols to olefins. These microporous materials have crystal frameworks comprised of $AlO_2$ and $PO_2$ tetrahedral units and tetrahedral oxide units of other elements, most commonly silicon or silicon and one or more divalent or polyvalent metals. Of these so-called non-zeolitic molecular sieves, the most thoroughly investigated as catalysts for the methanol-to-olefins conversion reaction have been the silicoaluminophosphates or SAPO's. In U.S. Pat. No. 4,499,327 any known member of the SAPO-n subclass of aluminophosphates is proposed as being suitably employed, but a preference is stated for those SAPO species having pores large enough to adsorb xenon, but small enough to exclude isobutane. More preferred are those SAPO species in which the pores are large enough to exclude isobutane but admit n-hexane into the pore system. The species denominated SAPO-34 is among those of the most preferred group.

One of the most important embodiments of the methanol-to-olefins conversion process is directed to he production of light olefins, i.e.,. olefins containing from 2 to 4 carbon atoms, inclusive. Accordingly, it is important to utilize a catalyst which maximizes the production of these products, results in a high degree of conversion of the starting methanol, and does not deactivate rapidly under the process conditions imposed.

SUMMARY OF THE INVENTION

It has been discovered that all of the aforesaid advantageous attributes of a methanol-to-olefin catalyst can be realized in a silicoaluminophosphate catalyst, preferably one having the crystal structure of SAPO-34, and which has been subjected to hydrothermal treatment with at least 5 psia steam at a temperature of at least 700° C. for a period of time sufficient to reduce the acidic sites per cc micropore volume to a number corresponding to less than $3.0 \times 10^{-3}$ mole of $NH_3$ while maintaining a degree of crystallinity of at least 80 percent. This finding is quite surprising in view of the fact that the loss of acidity would be expected to have a very deleterious effect upon catalyst life.

In carrying out the methanol conversion process the methanol is brought into contact with the silicoaluminophosphate catalyst in either the vapor or liquid phase using conventional operating conditions, i.e., a temperature between about 200° C. and 700° C., a pressure of between 0.1 and 100 atmospheres and a weight hourly space velocity, WHSV, of 0.01 to 100 hr.$^{-1}$.

DETAILED DESCRIPTION OF THE INVENTION

For use in the practice of the present invention, the catalyst is prepared from a starting silicoaluminophosphate molecular sieve consisting essentially of the tetrahedral framework structural units, $AlO_2$, $PO_2$ and $SiO_2$, and having an empirical formula in terms of mole fractions of silicon, aluminum and phosphorus based on the total content of those three elements of:

$$mR:(Si_xAl_yP_z)O_2$$

wherein "R" at east one organic templating agent present TM = the intracrystalline pore system; "m" represents the moles of "R" present per mole of $(Si_xAl_yP_z)O_2$ and has a value of zero to about 0.3; "x," "y" and "z" represent the mole fractions, respectively, of silicon, aluminum and phosphorus, "x" has a minimum value of 0.08; "y" has a minimum value of 0.40 and "z" has a value of at least 0.27. One example of such a silicoaluminophosphate is SAPO-34, which has a characteristic x-ray powder diffraction pattern containing at least the d-spacings set forth in Table I below:

TABLE I

| 2θ | d.A | Relative Intensity |
|---|---|---|
| 9.45–9.65 | 9.36–9.17 | s–vs |
| 16.0–16.2 | 5.54–5.47 | w–m |
| 17.85–18.15 | 4.97–4.89 | w–s |
| 20.55–20.9 | 4.32–4.25 | m–vs |
| 24.95–25.4 | 3.57–3.51 | w–s |
| 30.5–30.7 | 2.93–2.91 | w–s |

The notations, vs, s, m and w, represent very strong, strong, medium and weak, respectively. The SAPO-34 molecular sieves, i.e., those which contain only $AlO_2$, $PO_2$ and $SiO_2$ tetrahedral units, are preferably employed as the starting material in the preparation of the catalysts of the present invention. A detailed description of SAPO-34 and the method for its synthesis are set forth in U.S. Pat. No. 4,440,871, issued Apr. 3, 1984, and incorporated by reference herein in its entirety. It will be understood that up to 10% of the $TO_2$ units of the silicoaluminophosphate can be tetrahedral oxide units of other metal or metaloid elements such as Mg, Mn, Co, Zn, Fe, Ti, Cr, Ga, Ge, and B. Silicoaluminophosphates having one or more of these additional elements present in the form of framework oxide units are disclosed in U.S. Pat. No. 4,913,799, incorporated by reference herein in its entirety along with the disclosure of the reference disclosure referred to therein.

In carrying out the hydrothermal modification of the starting silicoaluminophosphate, it is preferred, but not essential, to first remove the organic template material present in the pore system as a result of the synthesis procedure. Usually the organic material comprises both occluded molecular species and organic charge-balancing cations in association with the $AlO_2$ tetrahedra not associated with charge-balancing $PO_2$ tetrahedra. The removal of organic species of either type is readily effected by calcination in air at temperatures of about 350° C. up to the crystal destruction temperature.

In either event, the crystalline silicoaluminophosphate composition is calcined in an atmosphere containing at least 2 psia steam at a temperature of at least 700° C. for a period of time determinable by reference to the number of acid sites remaining after steaming.

It is widely accepted in the art that the acidic sites in a crystalline silicoaluminophosphate molecular sieve are those associated with an $AlO_2$ tetrahedral unit not electrovalently balanced by the net positive charge of an appropriately situated $PO_2$ tetrahedron. The presence of such sites can be determined and their numbers indicated by observing the results of their reaction with basic species. For purposes of the present invention, an acidic site is defined as one which is capable of bonding with ammonia and retaining it in the chemisorbed state, at temperatures less than 300° C.

Accordingly, the SAPO composition is contacted by the steam-containing atmosphere at a temperature of from 700° C. to 900° C., preferably 725° C. to 775° C., until the number of acid sites per cc micropore volume is reduced to a number corresponding to less than $3.0 \times 10^{-1}$ mole $NH_3$, and preferably not more than $2.2 \times 10^{-3}$ mole $NH_3$, while retaining at least 80 percent of the crystallinity of the starting material. Such results are readily obtained using a temperature of 775° C. and a 100% steam atmosphere over the treatment period of at least 10 hours. For the determination of the retention of crystallinity, any of the methods well known in the art are suitable. One technique for assessing the crystallinity of the products relative to the crystallinity of the starting material is the comparison of the relative intensities of the x-ray diffraction peaks of the respective X-ray powder diffraction patterns. The sum of the peak heights, in terms of arbitrary units above background, of the starting material is used as the standard and is compared with the corresponding peak heights of the products. When, for example, the numerical sum of the peak heights of the product is 85 percent of the value of the sum of the peak heights of the starting zeolite, then 85 percent of the crystallinity has been retained. In practice it is common to utilize only a portion of the x-ray diffraction peaks for this purpose, as, for example, four or five of the six strongest peaks. In the case of SAPO-34 these d-spacings are those set forth in Table I, supra.

Other indicia of the crystallinity retained by the zeolite product are the degree of retention of surface area and the degree of retention of the adsorption capacity. Surface areas can be determined by the well known Brunauer-Emmett-Teller method (B-E-T) as described in J. Am. Chem. Soc. 60 309 (1938) using nitrogen as the adsorbate. In determining the adsorption capacity the capacity for oxygen at −183° C. at 100 torr is preferred.

Another method, and one we have used in connection with obtaining the data set forth in the working examples below, is the measurement of the micropore volume of the starting material and the final steam-modified SAPO product. The method for measuring the micropore volume is not critical and can be accomplished in accordance with any of the techniques well known in the art. For obtaining micropore volume data disclosed in the present specification, the t-plot method for quantitative analysis of the low pressure $N_2$ adsorption data has been used to determine micropore volume in cc/g. This method is described by M. F. L. Johnson in Journal of Catalysis, 52, p. 425–431 (1990) and is incorporated by reference herein. The change in crystallinity is assumed to be directly proportional to the change in micropore volume.

The acidic sites of the silicoaluminophosphate molecular sieves of significance to the present invention are located in the micropore system and are available to react with ammonia. In order to measure the acidic site population of the starting silicoaluminophosphate and of the hydrothermally treated product, the starting composition, after calcination at 600° C. under 1 atm. of helium to remove any residual water or organic species, is contacted with a mixture of ammonia and helium, preferably about 5 volume percent ammonia, at 1 atm. and ambient room temperature and allowed to equilibrate under the flow for several hours, preferably at least 3 hours. Temperature is then ramped to 650° C. at 10° C./min, with 40 cc/min. helium flow to desorb the ammonia which is quantitatively detected using a calibrated thermoconductivity detector. The amount of ammonia desorbed, between 300° C. and 600° C., is used as a measure of the acidic site population and when divided by the weight of the sample gives the number of acidic sites/gram. The number of acidic sites/cc micropore volume is then obtained by dividing this value by the micropore volume obtained by t-plot.

In converting methanol to olefins using the catalyst compositions of the invention, the process is preferably carried out in the vapor phase such that the feedstock is contacted in a vapor phase in a reaction zone with a silicoaluminophosphate molecular sieve at effective process conditions such as to produce light olefins, i.e., an effective temperature, pressure, WHSV (Weight Hourly Space Velocity) and, optionally, an effective amount of diluent, correlated to produce light olefins. Alternatively, the process may be carried out in a liquid phase. When the process is carried out in the liquid phase the process necessarily involves the separation of products formed in a liquid reaction media and can result in different conversions and selectivities of feedstock to product with respect to the relative ratios of the light olefin products as compared to that formed by the vapor phase process.

The temperature which may be employed in the process may vary over a wide range depending, at least in part, on the selected silicoaluminophosphate catalyst. In general, the process can be conducted at an effective temperature between about 200° C. and about 700° C., preferably between about 250° C. and about 600° C., and most preferably between about 300° C. and about 500° C. Temperatures outside the stated range are not excluded from the scope of this invention, although such do not fall within certain desirable embodiments of the invention. At the lower end of the temperature range and, thus, generally at the lower rate of reaction, the formation of the desired light olefin products may become markedly slow. At the upper end of the temperature range and beyond, the process may not form an optimum amount of light olefin products. Notwithstanding these factors, the reaction will still occur and the feedstock, at least in part, can be converted to the desired light olefin products at temperatures outside the range between about 200° C. and about 700° C.

The process is effectively carried out over a wide range of pressures including autogenous pressures. At pressures between about 0.001 atmospheres and about 1000 atmospheres, the formation of light olefin products will not necessarily form at all pressures. The preferred pressure is between about 0.01 atmospheres and about 100 atmospheres. The pressures referred to herein for the process are exclusive of the inert diluent, if any is present, and refer to the partial pressure of the feedstock as it relates to methanol. Pressures outside the stated range are not excluded from the scope of this invention, although such do not fall within certain desirable embodiments of the invention. At the lower and upper end of the pressure range, and beyond, the selectivities, conversions and/or rates to light olefin products may not occur at the optimum although light olefin products can be formed.

The process is effected for a period of time sufficient to produce the desired light olefin products. In general, the residence time employed to produce the desired product can vary from seconds to a number of hours. It will be readily appreciated by one skilled in the art that the residence time will be determined to a significant extent by the reaction temperature, the silicoaluminophosphate molecular sieve selected, the WHSV, the phase (liquid or vapor) selected and, perhaps, selected design characteristics.

The process is effectively carried out over a wide range of WHSV for the feedstock and is generally between about 0.01 hr$^{-1}$ and about 100 hr$^{-1}$ and preferably between about 0.1 hr$^{-1}$ and about 40 hr$^{-1}$. Values above 100 hr$^{-1}$ may be employed and are intended to be covered by the instant process, although such are not preferred.

The instant process is most preferably carried out under process conditions comprising a temperature between about 300° C. and about 500° C., a pressure between about 0.1 atmosphere (one atmosphere equals 14.7 psia) to about 100 atmospheres, utilizing a WHSV expressed in hr$^{-1}$ for each component of the feedstock having a value between about 0.1 and about 40. The temperature, pressure, and WHSV are each selected such that the effective process conditions, i.e., the effective temperature, pressure, and WHSV are employed in conjunction, i.e., correlated, with the selected silicoaluminophosphate molecular sieve and selected feedstock such that light olefin products are produced.

In addition to the presence of methanol in the feedstock, a diluent may be present in the feedstock in an amount between about 1 and about 99 molar percent based on the total number of moles of all feed components fed to the reaction zone (or catalyst). Typical of the diluents which may be employed in the instant process are helium, argon, nitrogen, carbon monoxide, carbon dioxide, hydrogen, water (steam), paraffins, hydrocarbons (such as methane and the like), aromatics (such as benzene, toluene, xylenes and the like), or mixtures thereof.

It has been discovered that the addition of a diluent to the feedstock prior to such being employed in the instant process is generally beneficial, although not required.

The instant process may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such silicoaluminophosphate molecular sieves in series to provide for a desired product mixture. Owing to the nature of the process, it may be desirous to carry out the instant process by use of the silicoaluminophosphates in a dynamic (e.g., fluidized or moving) bed system or any system of a variety of transport beds rather than in a fixed bed system. Such systems would readily provide for any regeneration (if required) of the silicoaluminophosphate molecular sieve catalyst after a given period of time. If regeneration is required, the silicoaluminophosphate molecular sieve catalyst can be continuously introduced as a moving bed to a regeneration zone where it can be regenerated, such as, for example, by removing carbonaceous materials by oxidation in an oxygen-containing atmosphere. In the preferred practice of the invention, the catalyst will be subject to a regeneration step by burning off carbonaceous deposits accumulated during reactions.

The invention is illustrated by means of the following Examples which are not be construed as being in any way limitative of the proper scope of the invention.

Example 1 (Preparation of SAPO-34 Catalyst)

A commercial scale lot of SAPO-34 was prepared as follows: 3195 lbs. of 85 weight % orthophosphoric acid was diluted with 9009 lbs. of water. To the resulting solution was added 566 lbs. of a commercially available reactive amorphous solid silica. During the course of the silica addition, vigorous stirring was employed to obtain a homogeneous dispersion. An aqueous solution of tetraethylammonium hydroxide (40 weight % TEAOH) in an amount of 2547 lbs. was then added to the silica disperison and the combined mixture stirred until homogeneous. Thereafter 2799 lbs. of di-n-propylamine was added and the mixture again stirred until homogeneous. Finally, 1883 lbs. of alumina (Versal-250, Kaiser Chemicals, Baton Rouge, La.) was added slowly with mixing to obtain a homogenous reaction mixture having a composition in terms of molar ratios of:

$$0.5\ TEAOH{:}2.0\ P_2O_5{:}Al_2O_3{:}0.6\ SiO_2{:}50\ H_2O$$

Crystallization was carried out at 175° C. with continuous agitation for 17 hours in a sealed reactor. The crystalline product was recovered by centrifugation and washed three times with an equal volume of water. The product was identified as SAPO-34 by x-ray analysis.

Example 2

(a) A SAPO-34 material prepared by a process similar to that set forth in Example 1 above and having a framework chemical composition in terms of mole fractions of $AlO_2$, $PO_2$ and $SiO_2$ tetrahedra of $(Si_{0.15}Al_{0.55}P_{0.30})O_2$ was formed into catalyst particles containing 40 weight percent SAPO-34, 40 weight percent kaolin and 20 weight percent silica. The SAPO-34 particles were initially milled to decrease to less than 100 mesh any particles having sizes of greater than 100 mesh. Thereafter the SAPO-34 particles were admixed with kaolin and an aqueous silica sol containing about 10.8 weight % $SiO_2$ and spray dried into agglomerate particles in the conventional manner. A 16.4 kilogram portion of the agglomerates was then slurried in 90 liters of water at 60° C., filtered and rinsed with additional water. Thereafter the spray dried particles were slurried in 90 liters of an aqueous $(NH_4)_2SO_4$ solution (containing 16.5 kilograms of ammonium sulfate) at a temperature of 60° C. for thirty minutes and recovered by filtration. This procedure was repeated twice again. The recovered solids were finally washed with 90 liters of water at 60° C., filtered and dried at 100° C. for about 14 hours. The dried product was calcined in air by raising the temperature from ambient room temperature to 550° C. over the period of two hours, held at 550° C. for 1.3 hours and then lowering the temperature to ambient room temperature over the period of 2 hours.

(b) The spray dried particles prepared in part (a) above were divided into four portions. The first portion was calcined in air at 650° C. for 3 hours and identified for further testing as Sample A. The second portion was calcined in an environment of 100% steam for 10 hours at 725° C. and identified as Sample B. The third portion was calcined in 100% steam for 10 hours at 775° C. and identified as Sample C. The last portion was calcined in 100% steam at 775° C. for 50 hours and identified as Sample D.

The four calcined products were analyzed to determine their micropore volume, the number of acidic sites in terms of meq. $NH_3$/cc and the x-ray crystallinity. The determined values are reported in tabular form below.

TABLE 2

| SAMPLE | HYDROTHERMAL TREATMENT | MICROOPORE VOLUME (cc/g) | meq $NH_3$/cc | % CRYSTALLINITY (BY MICROPORE VOLUME) |
|---|---|---|---|---|
| A | Air calcined 650° C., 3 hrs | .054 | 5.2 | 100 |
| B | 100% Steam 725° C., 10 hrs | .050 | 3.8 | 93 |
| C | 100% Steam 775° C., 10 hrs | .046 | 2.1 | 85 |
| D | 100% Steam 775° C., 50 hrs | .048 | 1.8 | 89 |

Example 3

The samples prepared in Example 2(b), above, were utilized in the conversion of a feedstock consisting of methanol, water and hydrogen in molar proportions respectively of 1/5.3/4.6. In each case the sample catalyst was loaded into a ⅜" I.D. ceramic-lined tubular reactor and the feedstock passed over the catalyst particles at 400° C. at a pressure of 5 psig and a methanol WHSV of 0.5 hr$^{-1}$. The reaction products were analyzed periodically during the runs to determine proportions of methane, propane and $C_2$-$C_5$ olefins. The analytical results are set forth in the tables below. Mole percent values reported have a tolerance of about ±1.0 mole %.

TABLE 3

| Hours on Stream | Selectivity for $C_2$ + $C_3$ Olefins, Mole % | | | |
|---|---|---|---|---|
| | Sample A | Sample B | Sample C | Sample D |
| 0.75 | 63 | 77 | 50 | 70 |
| 1.25 | 68 | 73 | 72 | 69 |
| 1.75 | 70 | 69 | 75 | 73 |
| 25 | 70 | 76 | 76 | 73 |
| 2.75 | 60 | 77 | 76 | 77 |
| 3.25 | 59 | 77 | 77 | 78 |
| 3.75 | 60 | 79 | 79 | 79 |
| 4.25 | — | 78 | 79 | 80 |
| 4.75 | — | 76 | 79 | 79 |

TABLE 3-continued

| Hours on Stream | Selectivity for $C_2$ + $C_3$ Olefins, Mole % | | | |
|---|---|---|---|---|
| | Sample A | Sample B | Sample C | Sample D |
| 5.25 | — | — | 77 | 81 |
| 5.75 | — | — | — | 79 |
| 6.25 | — | — | — | 80 |
| 6.75 | — | — | — | 81 |
| 7.25 | — | — | — | 80 |
| 7.75 | — | — | — | 80 |
| 8.25 | — | — | — | 80 |
| 8.75 | — | — | — | 79 |

TABLE 4

| Hours on Stream | Selectivity for $C_4$ + $C_5$ Olefins, Mole % | | | |
|---|---|---|---|---|
| | Sample A | Sample B | Sample C | Sample D |
| 0.75 | 19 | 21 | 22 | 22 |
| 1.25 | 17 | 14 | 18 | 23 |
| 1.75 | 14 | 16 | 17 | 21 |
| 2.25 | 14 | 16 | 16 | 22 |
| 2.75 | 12 | 17 | 18 | 18 |
| 3.25 | 5 | 14 | 16 | 17 |
| 3.75 | 5 | 13 | 16 | 17 |
| 4.25 | — | 16 | 14 | 17 |
| 4.75 | — | 18 | 15 | 19 |
| 5.25 | — | — | 16 | 18 |
| 5.75 | — | — | — | 18 |
| 6.25 | — | — | — | 18 |
| 6.75 | — | — | — | 15 |
| 7.25 | — | — | — | 17 |
| 7.75 | — | — | — | 16 |
| 8.25 | — | — | — | 16 |
| 8.75 | — | — | — | 18 |

TABLE 5

| Hours on Stream | Selectivity for Propane, Mole % | | | |
|---|---|---|---|---|
| | Sample A | Sample B | Sample C | Sample D |
| 0.75 | 14.5 | 9 | 9.5 | 6.5 |
| 1.25 | 12 | 10.5 | 6 | 6.5 |
| 1.75 | 12.5 | 12 | 5.5 | 6 |
| 2.25 | 11 | 6 | 5 | 4 |
| 2.75 | 11.5 | 5.5 | 3.5 | 3.5 |
| 3.25 | 10.5 | 6 | 3 | 2.5 |
| 3.75 | 7.5 | 5.5 | 4 | 2 |
| 4.25 | — | 4 | 3 | 2 |
| 4.75 | — | 3 | 3 | 1.5 |
| 5.25 | — | — | — | 2 |
| 5.75 | — | — | — | 1.5 |
| 6.25 | — | — | — | 1.5 |
| 6.75 | — | — | — | 2.5 |
| 7.25 | — | — | — | 2 |
| 7.75 | — | — | — | 2 |
| 8.25 | — | — | — | 2 |
| 8.75 | — | — | — | 1.5 |

TABLE 6

| Hours on Stream | Selectivity for Methane, Mole % | | | |
|---|---|---|---|---|
| | Sample A | Sample B | Sample C | Sample D |
| 0.75 | 1 | 1 | 1 | 1 |
| 1.25 | 1 | 1 | 1 | 1 |
| 1.75 | 1.5 | 1 | 1 | 1 |
| 2.25 | 2 | 1 | 1 | 1 |
| 2.75 | 7 | 1 | 1 | 1 |
| 3.25 | 11 | 1 | 1 | 1 |

TABLE 6-continued

| Hours on Stream | Selectivity for Methane, Mole % | | | |
|---|---|---|---|---|
| | Sample A | Sample B | Sample C | Sample D |
| 3.75 | 13.5 | 1 | 1 | 1 |
| 4.25 | — | 1 | 1 | 1 |
| 4.75 | — | 1.5 | 1 | 1 |
| 5.25 | — | — | 1.5 | 1.5 |
| 5.75 | — | — | — | 1.5 |
| 6.25 | — | — | — | 2 |
| 6.75 | — | — | — | 2 |
| 7.25 | — | — | — | 2 |
| 7.75 | — | — | — | 2 |
| 8.25 | — | — | — | 2.5 |
| 8.75 | — | — | — | 2.5 |

TABLE 7

| Hours on Stream | Methanol Conversion, % | | | |
|---|---|---|---|---|
| | Sample A | Sample B | Sample C | Sample D |
| 0.75 | 100 | 100 | 100 | 100 |
| 1.25 | 100 | 100 | 100 | 100 |
| 1.75 | 98 | 100 | 100 | 100 |
| 2.25 | 46 | 100 | 100 | 100 |
| 2.75 | 10 | 94 | 96 | 96 |
| 3.25 | 6 | 82 | 86 | 94 |
| 3.75 | 4 | 78 | 89 | 92 |
| 4.25 | — | 42 | 70 | 87 |
| 4.75 | — | 25 | 50 | 74 |
| 5.25 | — | — | 32 | 68 |
| 5.75 | — | — | 28 | 71 |
| 6.25 | — | — | — | 48 |
| 6.75 | — | — | — | 52 |
| 7.25 | — | — | — | 48 |
| 7.75 | — | — | — | 47 |
| 8.25 | — | — | — | 31 |
| 8.75 | — | — | — | 22 |

It is apparent from the data of Table 3 through 7 that the modified silicoaluminophosphate catalysts of the present invention are superior to prior known SAPO-34 catalysts for the conversion of methanol to olefins. Not only do these catalysts deactivate more slowly in use and convert a higher percentage of the feedstock, but they also produce less of undesirable methane and propane products and more of the desirable light olefins, particularly the $C_2$-$C_3$ olefins.

While the invention has been described and illustrated with respect to the silicoaluminophosphates having the SAPO-34 crystal structure, the principles involved in the modification procedure are equally applicable to silicoaluminophosphates of other crystal types. While the particular structure of SAPO-34 appears to be uniquely suitable for methanol-to-olefin conversions, the hydrothermal modifications improve the catalytic properties of the other SAPO structures in this regard.

What is claimed is:

1. Catalyst composition suitable for use in the catalytic conversion of methanol to light olefins comprising a crystalline silicoaluminophosphate molecular sieve prepared by the process of hydrothermally treating a silicoaluminophosphate having an empirical formula in terms of mole fractions of silicon, aluminum and phosphorus based on the total content of silicon, aluminum and phosphorus of $$mR:(Si_xAl_yP_z)O_2$$

wherein "R" represents at least one organic templating agent present in the intracrystalline pore system; "m" represents the moles of "R" present per mole of framework tetrahedral oxide units per mole of $(Si_xAl_yP_2)O_2$ and has a value of zero to about 0.3; "x," "y" and "z" represent the mole fractions, respectively, of silicon, aluminum and phosphorus, "x" has a minimum value of 0.08; "y" has a minimum value of 0.40 and "z" has a value of at least 0.27 with at least 2 psia water vapor at a temperature of at least 700° C. for a period of time sufficient to reduce its acidic sites per cc of micropore volume to a number corresponding to $3.0 \times 10^{-3}$ mole of $NH_3$ while maintaining a degree of crystallinity of at least 80%.

2. Catalyst composition according to claim 1 wherein the silicoaluminophosphate subjected to hydrothermal treatment has the crystal structure of SAPO-34.

3. Catalyst composition according to claim 1 wherein the silicoaluminophosphate subjected to hydrothermal treatment is SAPO-34.

4. Catalyst composition according to claim 1 wherein the hydrothermal treatment of the silicoaluminophosphate is for a time sufficient to reduce its acidic sites per cc micropore volume to less than the number corresponding to $2.2 \times 10^{-3}$ mole of $NH_3$.

* * * * *